April 30, 1940. G. H. STARR Plant Pat. 384

DOUBLE GYPSOPHILA

Filed May 8, 1939 2 Sheets-Sheet 1

Inventor
George H. Starr

By Rummler, Rummler & Woodworth Attys.

April 30, 1940. G. H. STARR Plant Pat. 384
DOUBLE GYPSOPHILA
Filed May 8, 1939 2 Sheets-Sheet 2
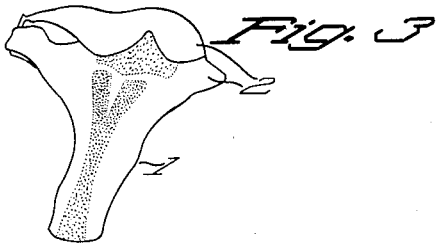
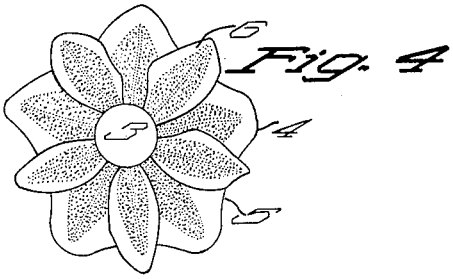
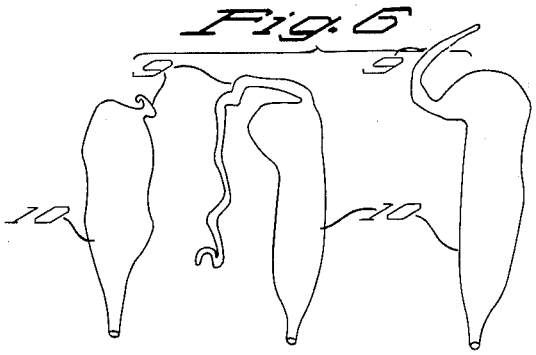
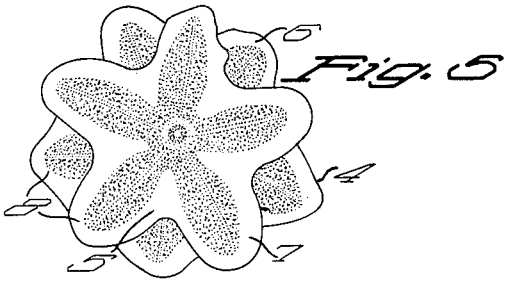
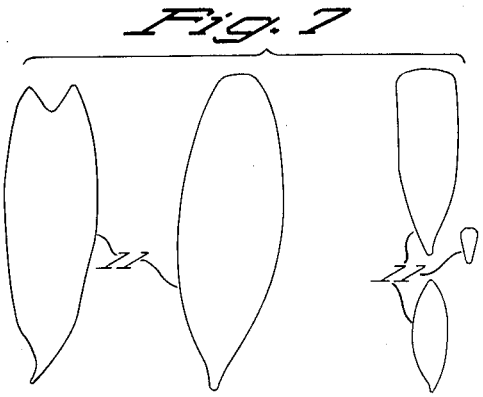
Inventor
George H. Starr
By Rummler, Rummler & Hoodworth Attys.

Patented Apr. 30, 1940

Plant Pat. 384

UNITED STATES PATENT OFFICE

384

DOUBLE GYPSOPHILA

George H. Starr, Turlock, Calif.

Application May 8, 1939, Serial No. 272,347

1 Claim. (Cl. 47—60)

The plant relating to a new and distinct vegetative variety of perennial Gypsophila, herein described, was developed during a definitely planned and extensive breeding and selecting period of fifteen years duration until the present type was fixed. The original population was about one-half an acre of *Gypsophila paniculata* Linn., *G. acutifòlia* Fisch and *G. rèpens* Linn. All of these species were heavy seeders, being exceedingly fertile. Seeds were gathered and planted in a new plot the second year from individuals of the *G. paniculata* population. One plant from this population was found not only to have a doubling of peals but to have registered many vegetative characters foreign to the species known as *G. paniculata* and common to the variety herein described.

It is assumed that the characters shown by this plant could only have been caused by hybridization with one of the species (*rèpens* or *acutifòlia*) which were grown with the *paniculata* population. It is still doubtful which one of these species could have crossed with the *paniculata* individual as no specific characters of either plant were assumed by the new individual. It is further assumed that the well-known genetical plasticity due to the complete hybridization of this individual caused the mutation in the floral parts, doubling the number of petals; thus it can be seen that the base stock for the variety in question was no doubt due to a rather complete hybridization of an individual of *G. paniculata* with either *G. acutifòlia* or *G. rèpens* and in addition to a simultaneous mutation in the floral parts, the result being a simple double flower with a departure from any species in question, of the vegetative characteristics, the departure of any one characteristic varying in greater or lesser degree from the homologous character in *G. paniculata*.

The seed from this plant was saved and a large population planted in which the majority were single flowered. There was a sufficient number of doubles, however, for crossing—all of which were fertile. Here the phenomenon of decreasing fertility took place, however, and continued to the fixation of the variety. The very vigorous fertility characterizing the base stock took a sudden drop and only about five per cent of the seeds of a plant was fertile. These double populations were extremely variable, both in floral and vegetative characteristics. In succeeding generations a rather large number of individual plants was soon found with more than double flowers. Three, four and five layers of petals were found combined with varying vegetative characteristics.

In the course of fifteen years of breeding several distinct stocks were selected both for floral and vegetative characteristics. One of these, having a lavender or purple flower, was propagated for a time and then bred out of the population but evidences of its influence still show up at various times in the fixed type, especially in very hot dry weather when some of the veins of the peals turn purple. Propagation by root dividing was resorted to and finally all attempts to gather seeds were abandoned and all seeded stocks were discarded in favor of one unique, seedless type combining the most favorable features of all. Grafting was resorted to as a means of propagation, the shoots from the crown of the fixed type being grafted to a seedling root grown for the purpose.

The plant was developed over a period of years with another object in view of obtaining flowers that would come into bloom all at one time, so that when harvesting one operation only is necessary; thus saving much labor. The main crop of flowers blooms in June and a second crop blooms from September to frost. The product is grown exclusively for sale as a dried flower.

Figure 2:
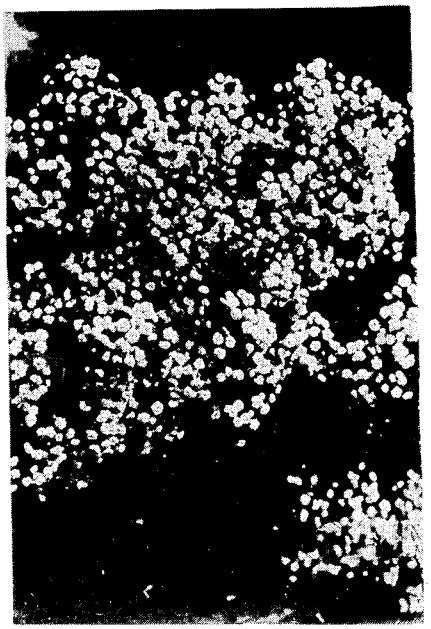
Fig. 2 is an enlarged view of a spray.
Figure 1:
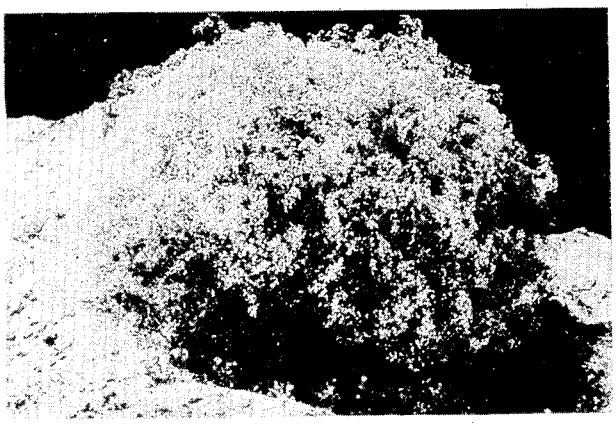
Figure 1 is a picture of one of the growing plants.

Figs. 3 to 5 inclusive illustrate in diagram the appearance of portions of a bloom as follows:

Fig. 3 shows the flower removed from its receptacle.

Fig. 4 is a plan view of the calyx indicating the receptacle in the center from which the flower was removed; and Fig. 5 is a basal view of the calyx indicating at the center by a small circle where the pedicel was removed.

Fig. 6 shows three variations in the pistil and ovary of different flowers.

Fig. 7 illustrates various types of petals found in the flowers.

Color is not a distinctive feature of the flower.

In the drawings, the flower is indicated by the numeral 1; petals thereof being numbered 2; the receptacle from which the flower is removed is numbered 3; the calyx is numbered 4. Of the calyx the basal layer of sepals is numbered 5; the inner layer of sepals is numbered 6. Calyx segments are shown at 7 and the scarious margins thereof at 8. The pistils and ovaries of the flower are respectively numbered 9 and 10 in Fig. 6. Various types of petals in the flower are indicated by 11, Fig. 7.

One characteristic which distinguishes this new flower from other varieties of double Gypsophila is the double-doubleness of the bloom. Each panicle contains from 4 to 8 double flowers within itself. These flowers form a compact head growing closer together than other varieties and, there being a number of double flowers in one flower, when dried the flower does not close up as do other varieties. The peduncles are more wiry and tougher than other varieties of Gypsophila; therefore they hold the flowers erect at all times. The foliage is similar to *Gypsophila paniculata.*

The following is a detailed description of the flowers when green and when dried:

Plant grafted in January, 1936, set out in April, 1936, on McCourt Place, Turlock, Calif., the stems and calyx all green:

| | | |
|---|---|---|
| Weight of plant | lbs | 12.5 |
| Number of stems | | 55 |
| Number of large stems | | 34 |

Five 2¼ pound bunches were made when dried from this plant with one pound left over.

Weight of 5 bunches when dry, 50.5 ounces. (Average weight approximately 10 ounces.)

Plant granted in January, 1937, set out in April, 1937, on Fickle Place, Turlock, Calif., the stems and calyx all green:

| | | |
|---|---|---|
| Weight of plant | lbs | 7.5 |
| Number of stems | | 25 |
| Number of long stems | | 14 |

Three 2¼ lb. bunches were made from this plant with ½ pound left over.

Weight of 3 bunches when dry, 31.5 ounces.

The plant is glabrous but sometimes pubescent in the lower portion. The stems are slender, erect, and much branched. The plant measures from 2 to 3 feet from root crown.

The leaves are lanceolate and opposite. The leaves on the stem are about 40 mm. long, 5 mm. wide; are acuminate at the apex, narrowed at the base. The leaves on the branches are much smaller, the bracts and bractlets minute. The pedicels are approximately 10 mm. long.

The flowers are white when ready to pick but if left on the plant a little too long and if the temperatures are above 90°, the flowers take on a slightly lavender or pink tinge.

The flowers average 8 mm. in breadth and are compact and numerous in the panicled cymes. The pedicels are terminated by floral proliferations, each one of which is subtended by two series of calyx-segments. The two series are alternate and adherent about one-third the distance from the basal center. The outer series is united almost to the middle, resembling an involucre. The inner set may or may not be united. In both sets each calyx-segment is broadly lobed and has broadly scarious margins.

The involucre-like calyx bears a central perfect flower and usually eight radiating sterile flowers. This central flower is hypogynous and is composed of five petals or petal-like structures which are united about two-thirds of the way and are usually green or pinkish-green in color with scarious margins. Sometimes one petal is larger and overlaps the others; the whole forming a closed tube completely enclosing the androecium and gynoecium.

The petals are white in color when the blossom is ready to pick; and sometimes have pink or lavender splotches along the mid-vein. The petals are about 2.5 mm. in length to extremely small. In shape they are oblong-linear, are cleft, rounded, or frilled at the apex and clawed at the base. Usually there are over 200 fully developed petals in each entire flower or proliferation, besides innumerable smaller ones. This gives the full flower a puff-ball or pincushion-like appearance, 7 to 8 mm. in diameter and 4 to 5 mm. in thickness.

The ovary is cylindrical, superior and not more than 2 mm. long, terminated by pistils of widely varying lengths, from a mere tubercle on the surface of the ovary to a long winding or coiled structure. Surrounding the ovary are four or five rudimentary stamens, less than 1 mm. long. These stamens appear to be rudimentary, as the plant does not seed and propagation must take place by grafting young shoots on seedling roots.

The lateral sterile flowers are born on pedicels a millimeter or more in length and variously branched. Sometimes the pedicels are united and may bear petals along their entire length which finally form a large cluster from which the pedicel may rebranch. Each branch is terminated by a small cluster of petals with an active growing point.

I claim:

The new and distinct variety of Gypsophila plant herein shown and described, characterized particularly by its prolific production of double flowers in one blossom, sterility, the substantially simultaneous blooming of the flowers of each plant in the crop permitting a common harvest, and exceptionally good keeping qualities when dried.

GEORGE H. STARR.